US012758404B2

(12) United States Patent
Haslinger et al.

(10) Patent No.: US 12,758,404 B2
(45) Date of Patent: Oct. 13, 2026

(54) PROSTHETIC WRIST

(71) Applicant: OTTO BOCK HEALTHCARE PRODUCTS GMBH, Vienna (AT)

(72) Inventors: Martin Haslinger, Vienna (AT); Felix Mittelberger, Vienna (AT); Luis Sagmeister, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 329 days.

(21) Appl. No.: 18/706,578

(22) PCT Filed: Nov. 17, 2022

(86) PCT No.: PCT/EP2022/082272
§ 371 (c)(1),
(2) Date: May 1, 2024

(87) PCT Pub. No.: WO2023/094259
PCT Pub. Date: Jun. 1, 2023

(65) Prior Publication Data
US 2025/0009527 A1 Jan. 9, 2025

(30) Foreign Application Priority Data
Nov. 23, 2021 (DE) ..................... 10 2021 130 659.0

(51) Int. Cl.
*A61F 2/58* (2006.01)
*A61F 2/50* (2006.01)
*A61F 2/68* (2006.01)

(52) U.S. Cl.
CPC ...... *A61F 2/585* (2013.01); *A61F 2002/5018* (2013.01); *A61F 2002/5075* (2013.01); *A61F 2002/6854* (2013.01)

(58) Field of Classification Search
CPC .. A61F 2/583; A61F 2/585; A61F 2002/5018; A61F 2002/5075; A61F 2002/6854
See application file for complete search history.

(56) References Cited

U.S. PATENT DOCUMENTS 4,636,221 A 1/1987 Kemp
8,795,387 B1 8/2014 Razink
(Continued)

FOREIGN PATENT DOCUMENTS

CN 110353865 A 10/2019
DE 845 095 B 7/1952
(Continued)

*Primary Examiner* — Bruce E Snow
(74) *Attorney, Agent, or Firm* — WCF IP

(57) ABSTRACT

The invention relates to a prosthetic wrist having a base for fastening to a proximal prosthesis component and having a pivot part which is mounted on the base in such a way as to be pivotable about a pivot axis,—having at least one fastening device for securing a distal prosthesis component or prosthetic hand to the pivot part, wherein—at least one catch segment with form-fit elements arranged thereon is arranged on the pivot part, and—at least one locking element is mounted on the base in such a way as to be longitudinally displaceable along the pivot axis, which locking element can be brought from a locking position, in which the locking element is in engagement with a form-fit element of the catch segment, counter to a spring force into a release position, wherein the locking element has two release regions with which a first and a second release position are realized, the first release region being arranged spaced apart from the second release region in the direction of displacement, and the second release region being assigned a catch element which holds the locking element in the second release position.

18 Claims, 8 Drawing Sheets

(56) References Cited

U.S. PATENT DOCUMENTS

Figure 1:
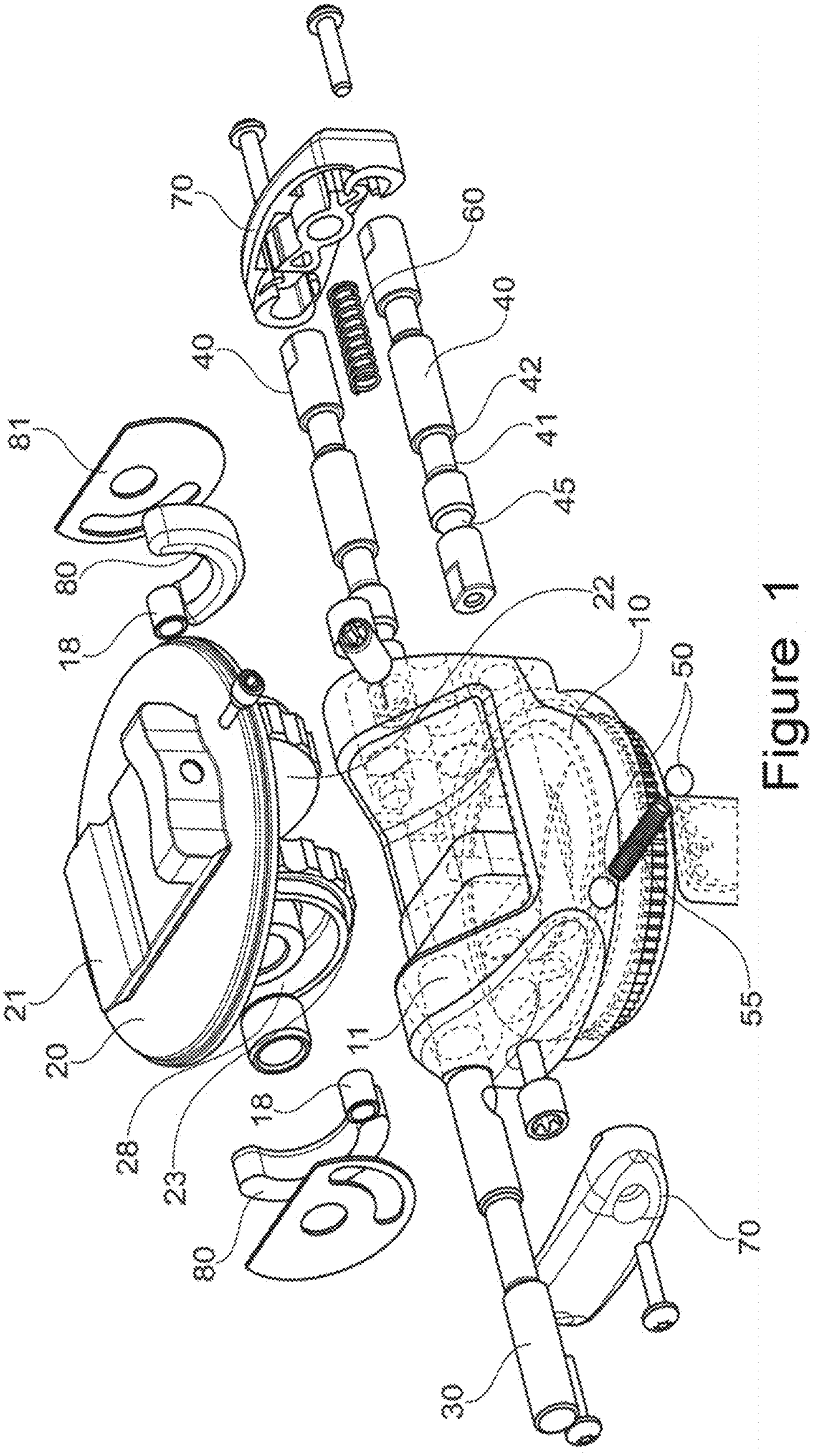

| | | | |
|---|---|---|---|
| 2007/0173955 | A1 | 7/2007 | Archer et al. |
| 2007/0260328 | A1 | 11/2007 | Bertels et al. |

FOREIGN PATENT DOCUMENTS

| | | | |
|---|---|---|---|
| DE | 3509879 | A1 | 9/1985 |
| DE | 10 2006 020 777 | A1 | 11/2007 |
| DE | 10 2006 020 777 | B4 | 8/2010 |
| EP | 1 852 092 | A1 | 11/2007 |
| WO | 2020/065265 | A1 | 4/2020 |

PROSTHETIC WRIST

The invention relates to a prosthetic wrist having a base for fastening to a proximal prosthesis component and a pivot part which is mounted on the base in such a way that it can pivot about a pivot axle, having at least one fastening device for securing a distal prosthesis component or prosthetic hand to the pivot part, wherein at least one catch segment with form-fit elements arranged thereon is arranged on the pivot part, and at least one locking element is mounted on the base in such a way that it can be longitudinally displaced along the pivot axle, wherein the locking element can be brought from a locked setting, in which the locking element is in engagement with a form-fit element of the catch segment, against a spring force into a release setting.

Prostheses replace limbs which are not present or no longer present. Prosthetic joints connect two components of a prosthetic device and allow these prosthesis components to pivot in relation to one another. Prosthetic joints in which two prosthesis components can be blocked from pivoting with respect to each other are known from the prior art. Depending on the construction of the prosthetic joints, the blocking or release takes place in different ways. If for example a resistance device, for example a hydraulic damper, is arranged between a joint upper part and a joint lower part, the relative movement between the upper part and the lower part may be achieved by blocking the hydraulic line. Another method of blocking and release takes place in the case of simple uniaxial joints by means of mechanical locks, with which the joints are fixed in their respective angular setting with respect to one another. If the lock is released and the distal prosthesis part is in an unlocked state, it is in general freely mobile. In prosthetic wrists, this may lead to the prosthetic hand being lowered or dropping in the direction of gravity.

DE 10 2006 020 777 B4 discloses a prosthetic wrist having a base and a coupling element assigned to the base for fastening to a body member or a prosthesis part and having a device for receiving a prosthetic hand, which device is connected to the base in such a way that it can pivot about at least one axle, with a locking device blocking the receiving device in relation to the base. A retaining element is resiliently prestressed against the receiving device and applies a holding force to the latter after the locking device is unlocked. The receiving device has latch elements into which the retaining element engages in a locked setting.

It is an object of the present invention to provide a prosthetic wrist that has a stable, robust and compact structure and provides increased flexibility for the user.

This object is achieved by a prosthetic wrist having the features of the main claim. Advantageous configurations and developments of the invention are disclosed in the dependent claims, the description and the figures.

The prosthetic wrist having a base for fastening to a proximal prosthesis component and a pivot part which is mounted on the base in such a way that it can pivot about a pivot axle, having at least one fastening device for securing a distal prosthesis component or prosthetic hand to the pivot part, wherein at least one catch segment with form-fit elements arranged thereon is arranged on the pivot part, and at least one locking element is mounted on the base in such a way that it can be longitudinally displaced along the pivot axle and can be brought from a locked setting, in which the locking element is in engagement with a form-fit element of the catch segment, against a spring force into a release setting, provides that the locking element has two release regions with which a first and a second release setting are implemented, that the first release region is arranged spaced apart from the second release region in the displacement direction, and that a catch element that holds the locking element in the second release setting is assigned to the second release region. By configuring the longitudinally displaceable locking element with two release regions, it is possible to bring the prosthetic wrist in a plurality of release settings into the release setting starting from the locked setting in which the locking element is in engagement with one of the form-fit elements of the catch segment. The spring force that acts against a shifting of the locking element from the locked setting into the release setting is applied by a spring element that is in engagement with the locking element. The locking element is displaced from the locked setting against the spring force into a first release setting along the direction of the longitudinal orientation of the pivot axle, until the first release region is positioned in such a way that the first release setting is obtained. In the first release setting, the pivot part can pivot relative to the base so that, for example, the prosthetic hand can be shifted from a neutral setting into an angled setting. If the actuation force against the spring force is then reduced or terminated, the locking element returns into the locked setting so that the prosthetic wrist remains in the adjusted setting and is locked therein with a form fit. If the locking element is moved into its second release setting, a catch element latches with the locking element or enters into engagement with the locking element, so that the catch element holds the locking element in the second release setting. In the second release setting, there is likewise no form-fit locking of the locking element with the catch segment, so that the pivot part has free or almost free mobility about the pivot axle. In addition, the locking element is permanently held by the catch element in the second release setting so that the prosthetic wrist is permanently freely mobile or almost freely mobile. This is advantageous, for example, when a prosthetic hand is placed flat on a table surface, when shaking hands or when patting on the back, since the wrist then appears to be acting naturally.

In one configuration, the locking element can be displaced from the first release setting into the second release setting against the spring force, so that the two release settings are arranged successively in the same displacement direction. The locking element is pushed from the release setting back into the locked setting by the spring force if the catch element is not, or no longer, in engagement and the reverse movement into the locked setting is blocked. It is thereby possible to configure the spring element for applying a spring force for example only as a compression spring, when the locking element is intended to be moved from the locked setting against the spring force into the release setting. Alternatively, it is possible that the first release setting requires displacement in a first displacement direction and the second release setting requires displacement of the locking element in the opposite direction. For this purpose, either two spring elements or one spring element which is configured as a tension spring element and compression spring element are provided.

In one configuration of the prosthetic wrist, the spring force against displacement into the second release setting is greater than the spring force against the displacement into the first release setting. The resistance behavior for a particular predetermined displacement path of the locking element from the locked setting into the first release setting lies at a first level, while the subsequent displacement path or the displacement path in the opposite direction entails a second resistance and requires a correspondingly increased restoring force, which is greater than the first resistance. Advantageously, the transition from the first resistance level to the second resistance level is significant, so that tactile feedback is provided during the actuation of the locking element.

In one configuration, the spring force against displacement into the second release setting at the start of the second release region is significantly greater, in particular 10% greater, than the spring force against the displacement of the first release region at the end of the first release setting.

In one configuration, the locking element is braced in relation to the base by means of at least one spring element against displacement into a release setting. The spring element may be configured in two stages, with a stepped or progressive spring characteristic, in order to provide the tactile difference in the displacement force to be applied against the spring prestress. Instead of this or in addition, a plurality of spring elements may be arranged in the displacement direction of the locking element in such a way that they can be brought successively into engagement, so that after the first release region has been reached, there is abruptly an increased resistance against displacement into the second release region by inter-engagement of a further spring element or further spring elements. In the case of a contrary movement in order to move the locking element from the locked setting into the first or second release setting, different spring strengths or resistances may be provided against displacement in the respective displacement direction. The resistances in the spring force preferably have a difference of more than 10% from one another in order to provide a clearly perceptible distinction between the release regions. The second release setting and the second resistance characterize the setting in which unlocking has taken place and pivoting about the pivot axle is possible, optionally against the restoring force that is applied by means of spring elements or elastomer elements. At this second, increased resistance level, when a corresponding position of the locking element has been reached, at least one catch element is brought into engagement or activated, so that restoring by the spring element into the first release setting or the locked setting is prevented.

The locking element may be assigned two actuation elements lying opposite one another in the displacement direction, so that the locking element can be displaced easily in both displacement directions along the longitudinal extent of the pivot axle.

Actuation into the first and second release settings as well as back from the second, locked release setting into the first release setting or locked setting is therefore readily possible.

In one configuration, two parallel-oriented locking elements are mounted on the base on either side of the pivot axle. The double configuration of the locking elements on either side of the pivot axle provides a reliable high catch function because of two catch axles with a comparatively high lever action with respect to the pivot axle.

The release regions of the locking element are configured in one configuration as flats or reductions in diameter of the locking element. In the region of the flats or reductions in diameter of the locking element or locking elements, the catch segments can pivot past the locking element.

In order to enable easy pivotability and functional capability in all settings, in one configuration the catch element is configured in the form of a circle segment and is fastened to or integrally formed on the pivot part.

A plurality of catch elements may also be fastened to or formed on the pivot part while being spaced apart from one another, in particular spaced apart from one another along the longitudinal extent of the pivot axle, in order to ensure reliable locking and uniform force absorption and force transmission.

In one configuration, the catch element is spring-loaded in the direction of the locking element, so that the catch element is latched or enters into engagement with the locking element automatically after the second release setting or the second release region has been reached, the locking element in one embodiment having a form-fit component, into form-fitting engagement with which the catch element can be brought.

The pivot part may be mounted on the base in such a way that it can pivot against a spring force, in order to be able to provide a certain restoring force into an initial position even in a release setting.

The pivot part may be held in an initial setting by means of at least one spring component acting in opposite directions, in particular by means of two oppositely acting spring components, or may be exposed to oppositely acting spring forces that move the pivot part in the direction of an initial setting or exert a force in the direction of the initial setting.

The spring components for applying a spring force in the direction of an initial setting may be arranged in recesses on the base or the pivot part, in particular the catch segment, and may be braced on abutments on the respectively opposite element. If the spring components are arranged in recesses on the base, the abutment is arranged on the pivot part, in particular the catch segment, and if the recesses are configured in the pivot part, particularly in a catch segment, the abutment on which the respective spring component is braced is arranged or formed on the base. The respective abutment may be configured as a bushing which is secured to the pivot part, in particular the catch segment, or to the base.

In one development, the spring component is assigned a stop on which the spring component bears, particularly in a prestressed state. The abutment bears on the spring component in a predetermined setting, for example in a neutral setting, and is arranged on the pivot part or the base in such a way that it can be shifted away from the stop by the spring component. The initiation force for pivoting from the neutral setting may thereby be adjusted, in particular increased, in order to achieve a stable setting.

Figure 2:
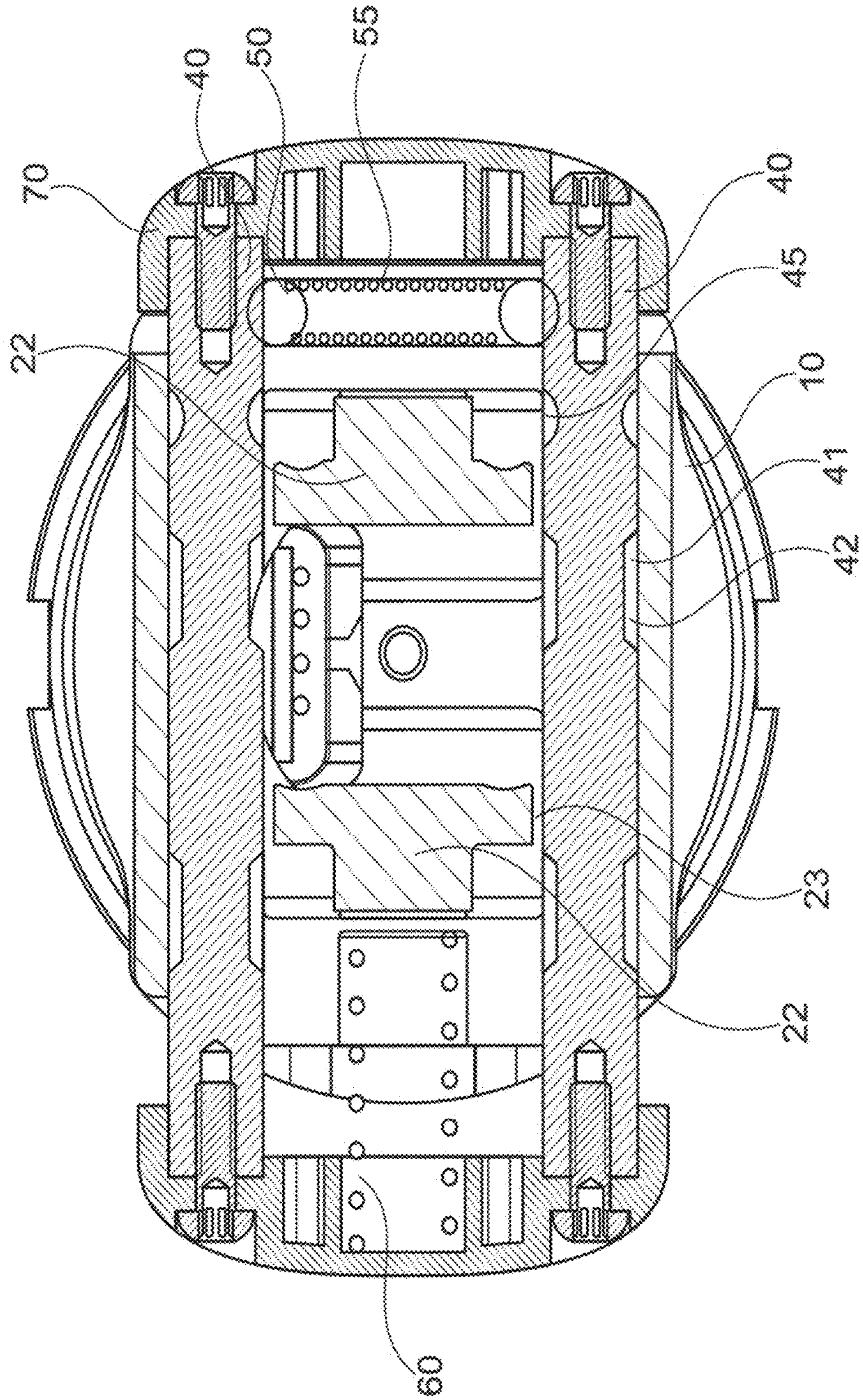
Figure 3:
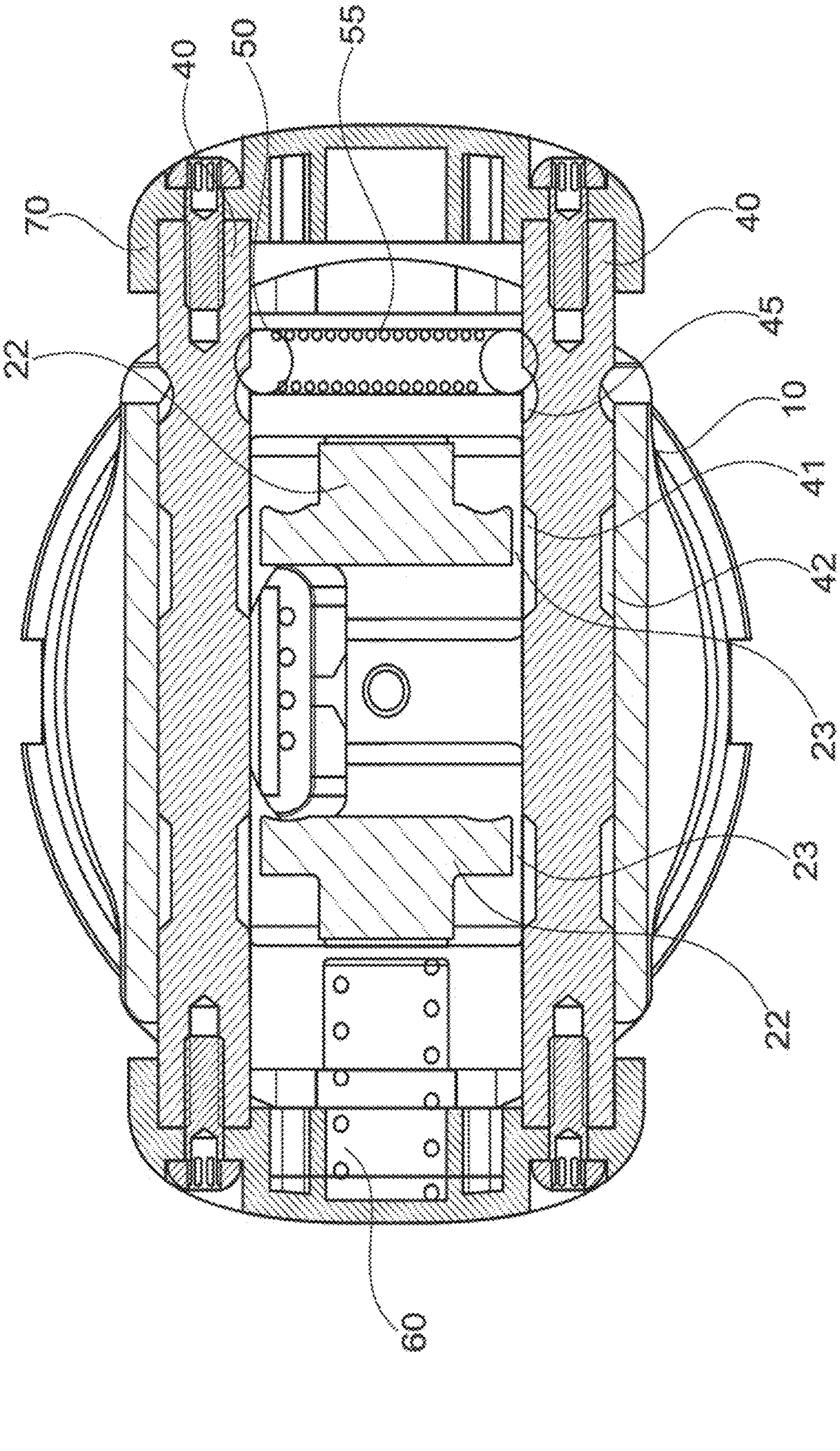
Figure 4:
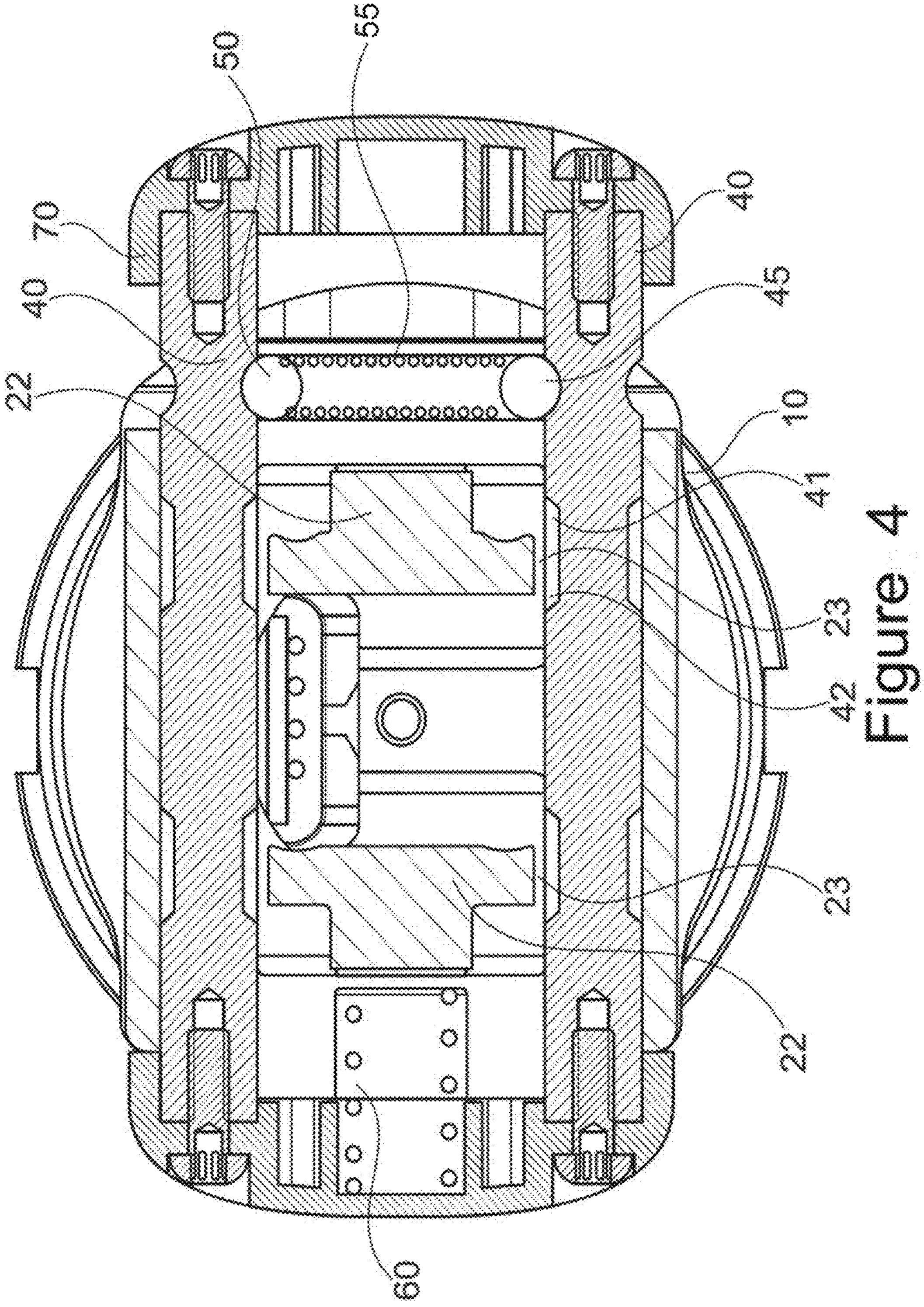
Figure 5:
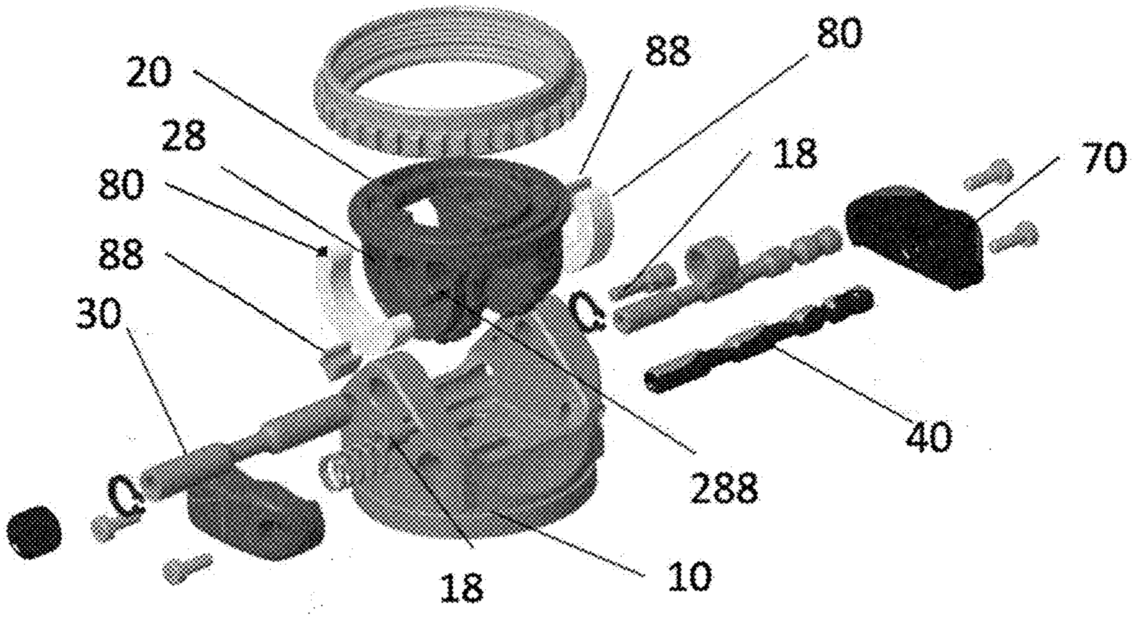
Figure 6:
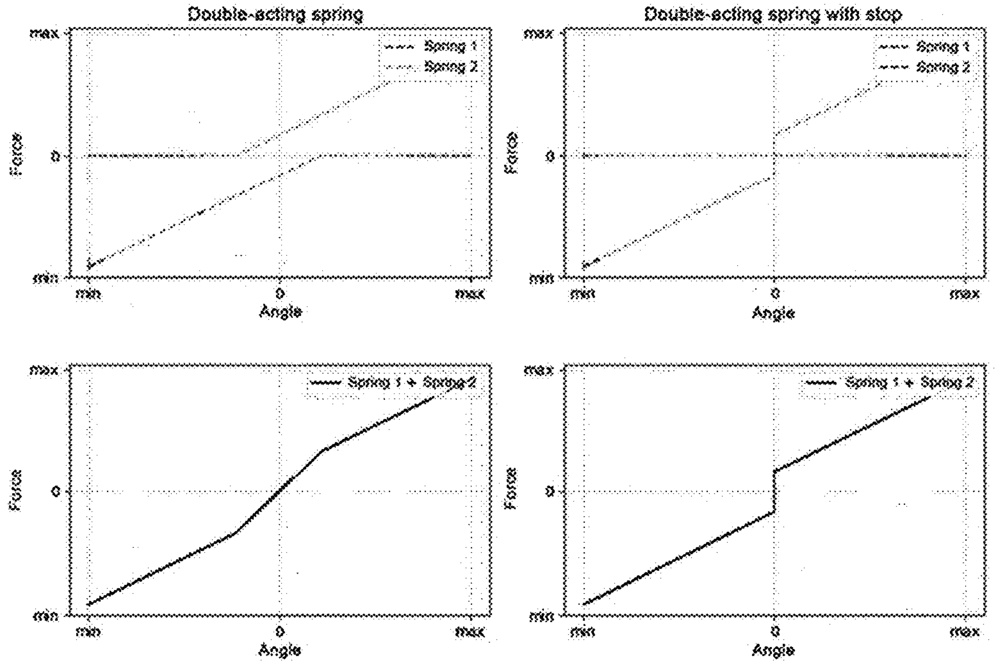
Figure 7:
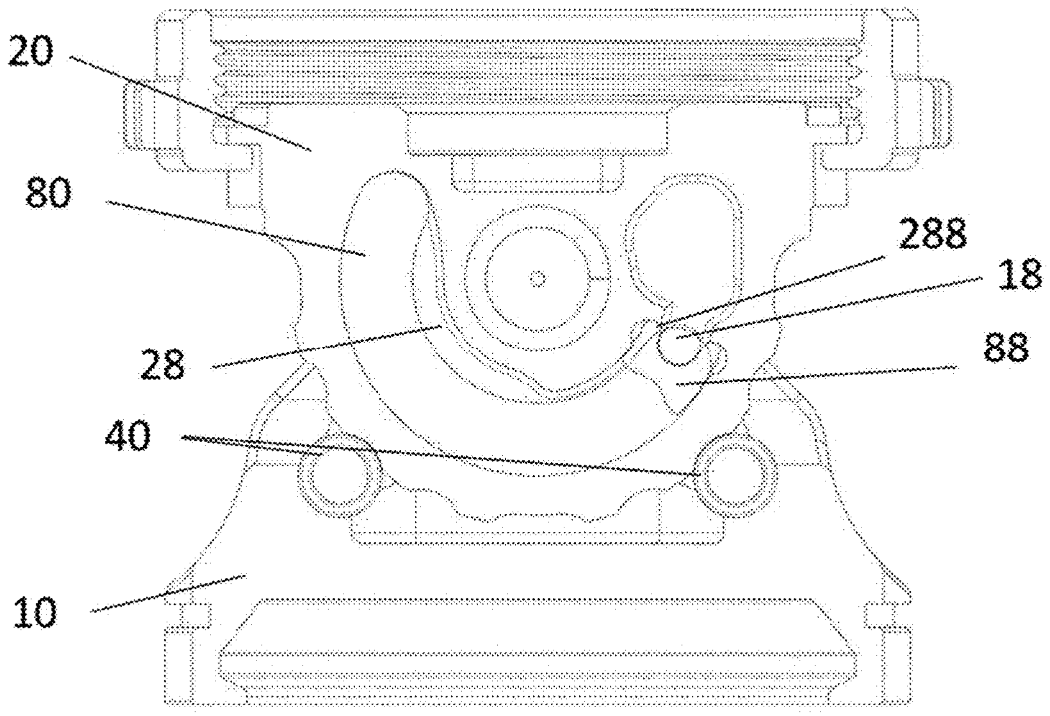
Figure 8:
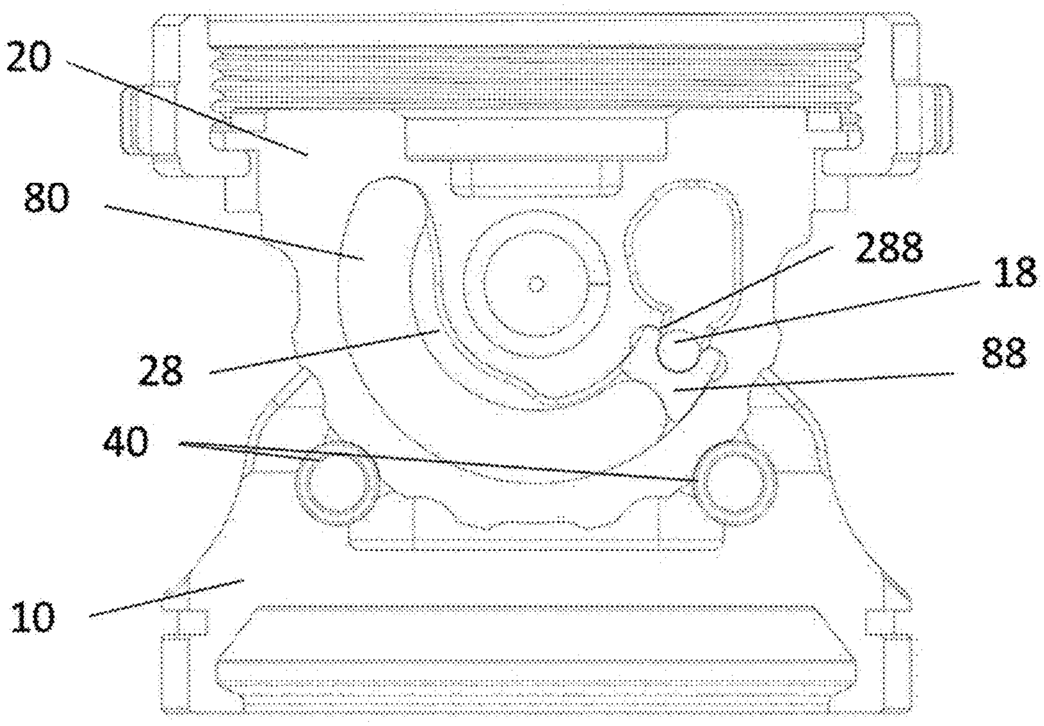
Figure 9:
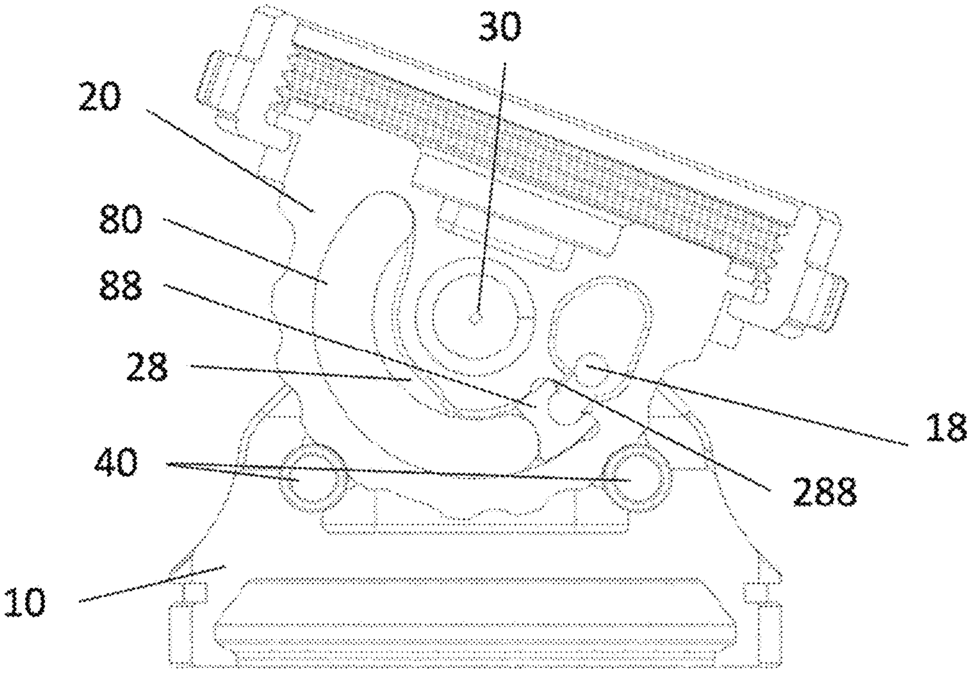
Figure 10:
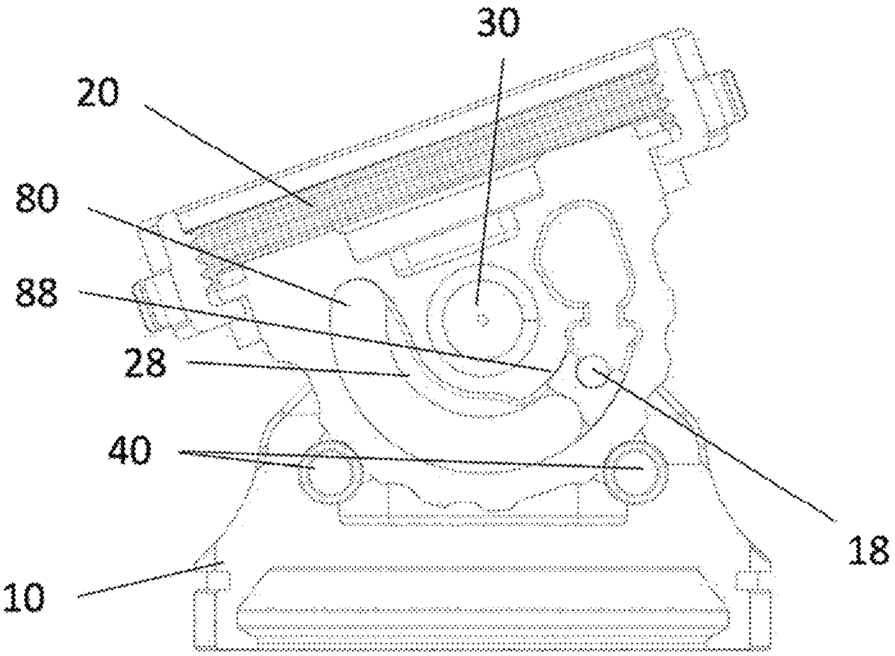

Exemplary embodiments of the invention will be explained below with the aid of the figures, in which:

FIG. 1—shows an exploded representation of a prosthetic wrist;

FIG. 2—shows a schematic view in a vertical section in the catch setting;

FIG. 3—shows a representation according to FIG. 2 in the first release setting;

FIG. 4—shows a representation according to FIG. 2 in the second release setting;

FIG. 5—a variant of FIG. 1;

FIG. 6—shows various spring characteristics;

FIG. 7—shows a side view according to FIG. 5;

FIGS. 8-10—show various settings of the prosthetic wrist; and

Figure 11:
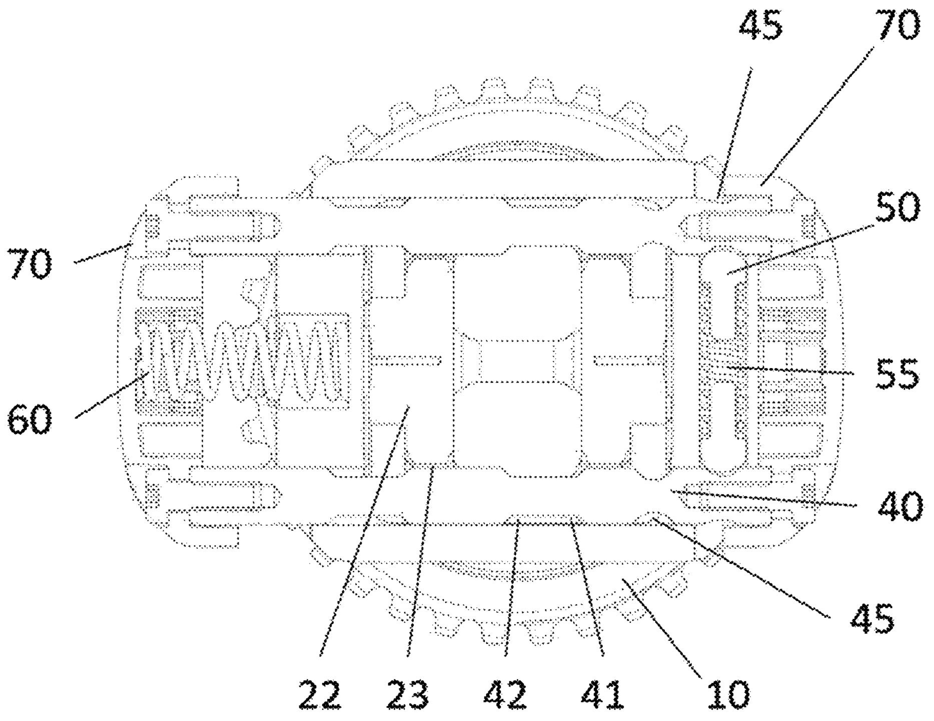
Figure 12:
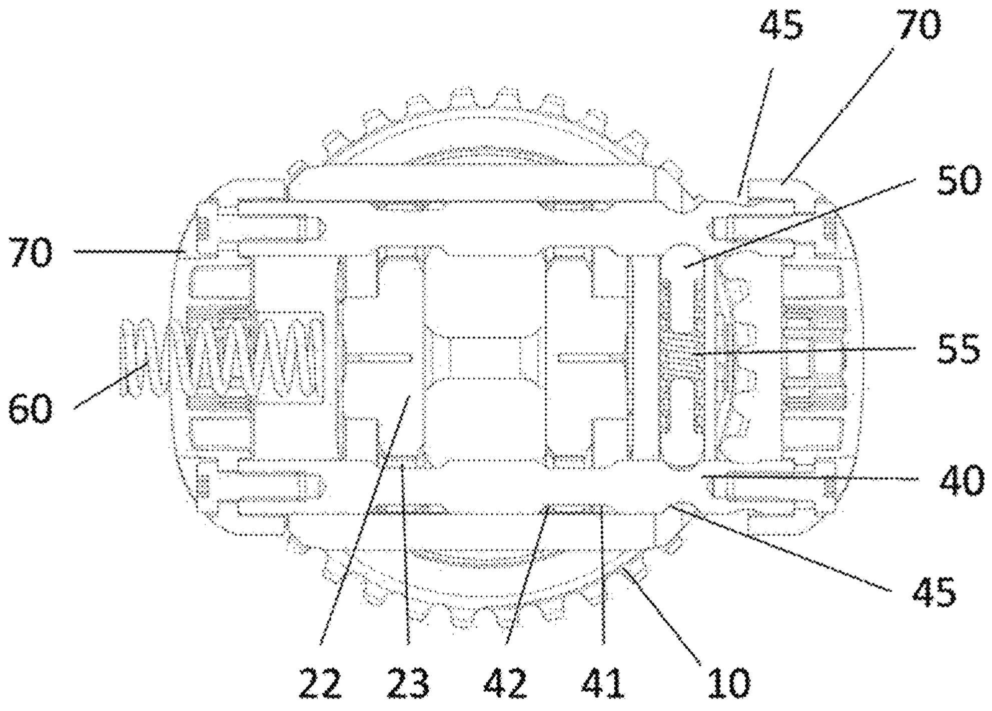

FIGS. 11 and 12—show variants of the catch mechanism.

FIG. 1 shows a perspective exploded representation of a prosthetic wrist with a base 10, on which a pivot part 20 is mounted between two mounting blocks 11 in such a way that it can be pivoted about a pivot axle 30. The two mounting blocks 11 extend in the distal direction from a bottom plate of the base 10. Arranged in the proximal direction from the bottom plate in the exemplary embodiment, there is a pivot bearing about which the prosthetic wrist can be fastened in such a way that it can be rotated on a forearm socket or a forearm tube. The base 10 is, in particular, configured in one piece or integrally. A free space, in which the pivot part 20 is arranged, is formed between the two mounting blocks 11. The pivot part 20 has a fastening device 21 on its distal upper side for securing a distal prosthesis component, in particular a prosthetic hand (not shown). The fastening device 21 in the exemplary embodiment represented is a dovetail guide, onto which a corresponding dovetail groove of the constituent part to be fastened can be fitted. Alternatively, the fastening device 21 is configured as a union nut, as will be explained below. Arranged on the opposite lower side from the fastening device 21, there are two catch segments 22 which are configured as disk-shaped protrusions in the form of circle segments and in the mounted state are arranged between the mounting blocks 11. Form-fit elements 23 in the form of protrusions and indentations are formed on the outer circumference of the catch segments 22, the form-fit elements 23 being in particular uniformly distributed over the circumference. The form-fit elements 23 on the two catch segments 22 arranged spaced apart axially from one another are aligned with one another so that stepwise setting and fixing, or release, can take place in the respectively desired position.

Two locking elements 40 in the form of longitudinally displaceable rods or bolts are mounted on the base 10 in the mounting blocks 11. The two locking elements 40 are aligned parallel to one another and run parallel to the longitudinal extent of the pivot axle 30. Actuation elements 70 in the form of pressure plates are arranged on the two end sides of the locking elements 40 and are connected to the locking elements 40 by means of screws. The locking elements 40 are braced in relation to the base 10 by means of a spring element 60 or a plurality of spring elements, so that shifting and displacement of the locking elements 40 takes place inside channels, which are formed in the base, against a spring force or a prestress.

The locking elements 40 in the embodiment represented are configured in the form of rods and have a substantially round cross section. Formed along the longitudinal extent of the locking elements 40, there are flats or reductions in diameter which can be brought into alignment with the respective catch segments 22 in the respective settings. The functionality will be explained below. The regions with a larger diameter are in engagement in a catch setting with the form-fit elements 23 on the catch segments 22. If the locking elements 40 are displaced, the regions with a larger diameter are brought out of engagement with the form-fit elements 23 so that the regions with the smaller diameter or with the material recesses lie opposite the form-fit elements 23. In the exemplary embodiment represented, two release regions 41, 42 for each catch segment 22 are formed on the respective locking element 40. The two release regions 41, 42 are divided into a first release region 41 and a second release region 42. The first release region 41 overlaps with the form-fit elements 23 of the respective catch segment 22 in a first release setting. This is directly followed by the second release region 42 in the axial displacement direction behind the first release region 41. In both release settings 41, 42, the locking elements 40 do not block the pivoting of the pivot element 20 about the pivot axle 30. In addition, a form-fit component 45 in the form of a circumferential groove is formed on the locking elements 40, which is arranged in such a way that a catch element 50 can enter into engagement with the form-fit component 45 in the second release setting and only in the second release setting. The catch element 50 is configured in the exemplary embodiment represented as a sphere, which is mounted inside the base 10 in a bore while being prestressed in the direction of the respective locking element 40 by means of a spring 55. The form-fit component 45 is formed at a distance from, and separated from, the release regions 41, 42 on the respective locking element 40.

In the assembled state, the catch elements 50 are in abutment on the locking elements 40 under prestress by the spring element 55. Since the two locking elements 40 oriented substantially parallel to one another are spaced apart equally on either side from the projection of the pivot axle 30 and the outer diameter outside the release regions 41, 42, and the form-fit component 45 enters into engagement with the protrusions of the form-fit elements 23, the pivoting movement of the pivot element 20 relative to the base 10 is blocked. The increased diameter regions or catch regions of the locking elements 40 can be displaced along the form-fit elements 23 or the recesses on the outer circumference of the catch elements 22 in the longitudinal direction against the spring force due to the spring 60. The prosthetic wrist in an initial setting is therefore in a catch setting or locked setting and is unblocked by pressing onto an actuation element 70 against the spring force 60. For this purpose, the locking elements 40 are shifted against the spring force 60 out of the catch setting or locked setting into a release setting. In the first release setting, it is possible for the pivot part 20 to pivot relative to the base 10 about the pivot axle 30. The pivot axle 30 is secured by means of a grub screw inside the mounting blocks 11 against rotation and against axial movement. In one alternative, the pivot axle 30 is configured in two parts, each half-axle being secured on each side by a grub screw. The pivot part 20 is mounted on mounting bushings on the pivot axle 30.

Recesses 28, which are respectively opened outward in the direction of the mounting blocks 11, are arranged on the outer sides of the catch elements 22. The recesses 28 are configured in the form of circle segments, for example semicircularly, and respectively receive a spring component 80. In the exemplary embodiment represented, the spring components 80 are configured in one piece and are formed as elastomer elements in a manner corresponding to the shape of the recess 28. The respective spring component 80 is braced in relation to the base 10 on abutments 18, which are arranged on opposite sides of the pivot axis 30 and are fixed to the base 10 on the mounting blocks 11 by means of screws or axles. During pivoting in the one direction starting from an initial setting, one spring component 80 is compressed, and the other is respectively compressed during pivoting starting from the initial setting in the other direction. Only one spring component 80 at a time is therefore compressed relative to the initial setting during pivoting from the initial setting. The spring components 80 may be configured in such a way that there is a basic stress, so that even in a release setting pivoting about the pivot axle 30 is possible only after overcoming a predetermined, preferably adjustable spring force.

As an alternative to the embodiment represented, the corresponding recess for the spring component 80 may also be formed in the mounting block 11 of the base, the abutment then being arranged or formed on the respective catch segment 22. The recesses 28 are covered outwardly by means of cover disks 81, in particular stainless steel disks. Links are formed inside the cover disks 81, so that the axles or pins, which lead from the mounting blocks 11 to the bushings as abutments 18, do not impede pivoting of the cover disks 81 with the pivot element 20.

By the spring components 80, it is possible to achieve a resilient initial setting or null setting. The counter-sense arrangement of the spring components 80 allows a uniform or different counter-force against pivoting from the initial setting. Besides protection against contamination, the cover disks 81 also serve to limit the volume of the recesses 28 so that, during a deformation of the spring components 80 configured as elastomer components, the latter are not pressed out of the recesses 28. Furthermore, the cover disks 81 serve to compensate for play. As an alternative to configuring the spring components 80 as elastomer elements, they may also be configured as coiled springs or spiral springs. The mounting of the elastomer components, in particular the semilunate elastomer elements, in correspondingly shaped recesses may be used even without the locking elements 40 with the release regions 41, 42 and the retaining or fixing in the second release setting, and is a further aspect of the invention that may also be pursued independently and separately.

The form-fit elements 23 in the exemplary embodiment are configured in the form of circle segments and define latch settings in which the orientation of the pivot part 20 relative to the base 10 may be secured. The locking elements 40 are advantageously configured so as to be round in cross section in the engagement regions, which leads to better surface pressure in the catch setting. It may be seen in FIG. 1 that lead-in chamfers are formed both on the catch segments 23 and on the locking elements 40, so that the locking elements 40 or catch pins can engage into the respective recess or the form-fit element 23 on the outer circumference of the catch segments 22 by the spring force of the spring 60. The spring 60 may be configured in two stages, progressively, conically or in multiple pieces.

FIG. 2 shows a plan view through a section in the plane of the locking elements 40 in the locked initial setting. The rod-shaped locking elements 40 are arranged parallel to one another and are mounted displaceably on the base 10 while being oriented on either side of the catch segments 22 parallel to the pivot axle (not represented). The spring element 60 is mounted with a prestress on the base 10 and on the actuation element 70, and exerts a prestress force in the direction of the catch setting represented. The locking elements 40 are in engagement with the form-fit elements 23 of the catch segments and prevent pivoting about the pivot axle. The catch elements 50 are prestressed by means of the spring 55 in the direction of the locking elements 40 and bear on the outer side of the locking elements 40, and permit displacement of the locking elements 40.

FIG. 3 represents the setting of the locking elements 40 after shifting to the right into a first release setting. The form-fit elements 23 of the catch segments 22 are now located opposite the first release region 41, which is configured as a region of a circumferential groove. The previously existing form-fit locking between the locking elements 40 and the catch segments 22 at four mutually opposite locations is now disengaged, so that the pivot part 20 can pivot against the spring force due to the spring components 80 about the pivot axle 30. The catch elements 50 in the form of the spheres continue to roll on the outer side of the locking elements 40 and are not yet in engagement with the form-fit component 45 of the locking element 40. If no further pressure force is applied from the left side against the spring 60 in this setting, the locking elements 40 move back into the initial setting according to FIG. 2. The first release setting represented is used to carry out intentional pivoting of the pivot part 20 in relation to the spring components 80 and then fix the prosthetic hand in this position by a return movement into the locked setting taking place automatically when a pressure force is no longer applied by the user.

If permanent release and pivotability against the spring components 80 is desired, a further displacement of the locking elements 40 to the right is carried out until the catch elements 50 latch into the form-fit components 45. This is represented in FIG. 4. The spring force of the spring 55 is adjusted in such a way that the second release setting according to FIG. 4 is maintained even after the termination of a displacement force against the spring 60. In this second release setting, the form-fit elements 23 of the catch elements 22 are still out of engagement with the locking elements 40 and are opposite the second release regions 42. The second release region 42 is positioned and selected in such a way that the catch element 50 latches into the form-fit component 45. In order to negate this permanent release setting, an actuation force acting to the left in the direction of the prestress force of the spring 60 is exerted, so that the catch elements 50 are shifted inward against the spring 55 and displacement of the locking elements 40 is brought about.

In order to make the transition from the first release region to the second release region perceptible for the user, a plurality of spring elements 60 may be provided, which enter into engagement successively so that an abrupt and perceptible increase in the resistance force occurs against displacement from the first release region into the second release region.

FIG. 5 shows a further embodiment of the prosthetic wrist, which corresponds substantially to the embodiment of FIG. 1. The same reference signs denote constituent parts that are the same. For reasons of clarity, not all references signs of FIG. 1 are also included in FIG. 5. The substantial difference between the embodiments of FIG. 1 and FIG. 5 is that the recesses 28, into which the curved spring components 80 are inserted, on the part 20 in the region of the catch elements are respectively provided with a stop 288, which in the embodiment represented is configured as a constriction. The stop 288 may also be configured as a separate component. The stop 288 may be arranged at various locations on the catch segment in the recess 28 or on the recess 28, in order to be able to adjust and vary the position of the stop 288. The spring component 80 is braced by means of a dog 88 on the respective abutment 18 that is fastened to the base 10. During pivoting, the abutments 18 pass through the constriction of the stop 288 or do not come in contact with the stop 288, when the pivoting of the pivot part 20 is performed about the pivot axle 30. Depending on the pivoting direction and the pivot setting, the respective abutments 18 are brought into engagement with the dog 88 or move freely without contact with the dog 88, when the abutments 18 are located between the protrusions of the stop 288 or away from the latter on the side facing away from the dog 88. The functionality will be explained further below.

FIG. 6 shows the spring characteristics of the individual spring components in the upper representation, the combined or resultant spring characteristic of the overall spring arrangement of the spring components 80 being represented in the respective lower representation. The left representation shows the spring characteristic of the double-acting spring components 80 according to FIG. 1, and the right representation shows the configuration with the dogs 88 and the stop 288 according to FIG. 5. In both embodiments, two spring components acting oppositely to one another are located between the base 10 and the pivot part 20, and these may also exert a damping function because of the configuration as elastomer components with solid-body damping.

The two abutments 18 for the mutually opposite spring components 80, which may for example be configured as mounting screws, are connected to the base 10 and protrude into the recesses 28 in which the spring components 80 as well as the dogs 88 are arranged. The abutments 18 transmit the spring force from the spring components onto the pivot part 20. The two spring components 80 are configured as compression springs, at least in the exemplary embodiments represented, and are prestressed in the neutral position in which no flexion or extension of the pivot part 20 is performed. The two spring components 80 act in opposite directions. Since the spring forces of the spring components 80 act in opposite directions, the resultant force is given by the difference of the two spring forces. An exemplary profile of the oppositely acting spring components 80 of FIG. 1 is represented in the left upper representation of FIG. 6. If the two spring components 80 transmit a force onto the base 10 to the same extent until complete relaxation, the spring forces thereby cancel each other out fully in the neutral position, or expressed the other way round, when the spring forces fully cancel out, the pivot part 20 is in the rest setting or neutral setting. The spring characteristic resulting from such an arrangement is shown in the lower left representation of FIG. 6. A significant restoring force can therefore be achieved only beyond a certain flexion angle or extension angle, so that there is a comparatively large play of the prosthetic wrist around the neutral setting.

In order to achieve greater stability of the pivot part 20 relative to the base 10, it is possible to dissipate and therefore neutralize the force of a spring component 80 only beyond a defined angle in the pivot part 20. A significantly higher restoring force may thereby be provided even with small deflections from the neutral position. A higher force is therefore required in order to deflect the pivot part 20 from the neutral position, or the prosthetic hand relative to the socket. This is achieved by the prestressed spring component 80 being provided with a high prestress in the respective active direction by means of the dog 88 and the abutment 18 being capable of being brought out of contact with the dog 88 in the opposite direction. The arrangement of a dog 88 has some advantages, it being for example possible that different materials may be employed by means of the separate dog 88. The dog 88 may be configured to be substantially stiffer or more rigid than the spring component 80, so that improved and more precise force transmission can take place from the base 10 via the abutment 18 onto the spring component 80. Both the abutment 18 and the dog 88 may consist of metal or a hard plastic, so that no deformation occurs upon contact of the abutment 18 with the dog 88. Furthermore, it is possible to adjust the spring retention of the spring components 80 by means of the replaceable dog 88. The larger the dog 88 is, the higher the compression and therefore the prestress of the spring components 80 are. In principle, it is however also possible to form the dog 88 as part of the spring component 80, or to configure the spring component 80 in such a way that the abutment 18 can be brought out of engagement with the spring component 80 by the spring component 80 bearing on the stop 288.

FIG. 7 shows a schematic side view of the prosthetic wrist according to FIG. 5 before the spring component 80 is introduced in the compressed state into the recess 28. The curved spring component 80 is placed in the identically or similarly curved recess 28 and extends as far as the taper that forms the stop 288. The taper inside the recess 28 is configured in such a way that the abutment 18 on the base 10 can pass through a channel or free space and enter the right, free end of the recess 28. In the neutral position represented, the spring component 80 is in an uncompressed state, the dog 88 is positioned lying in the position on the stop 288, and the abutment 18 bears in a recess in the dog 88.

In FIG. 8, the prosthetic wrist is fully mounted. The two spring components 80 are arranged on mutually opposite sides and are introduced inside the respective recess 28. The dog 88 is located between the stop 288 and the right end of the spring component 80. The abutment 18 protrudes into the recess 28 and can be moved in both directions, depending on the way in which the pivot part 20 is pivoted relative to the base 10 about the pivot axle. In this initial position, comparatively high forces are needed in order to shift the pivot part 20 counterclockwise because of the spring prestress of the spring components 80. Pivoting clockwise is not impeded by the spring component 80 represented, this being achieved by the spring component on the opposite side on the other catch segment.

FIG. 9 represents pivoting of the pivot part 20 clockwise about the pivot axle 30. The abutment 18 is brought out of engagement with the dog 88, which continues to be pressed against the stop 288 by the prestressed spring component 80. If, as represented in FIG. 10, the pivot part 20 is pivoted counterclockwise about the pivot axle 30, beyond the neutral setting which is represented in FIG. 8, the abutment 18 enters into engagement with the dog 88 and a resistance force against the pivoting is provided by the spring component 80. The initiation force for pivoting in one direction or the other may be adjusted according to the level of the prestress force. It is likewise possible to adjust different initiation forces, that is to say to provide a higher initiation force for extension than for flexion, or vice versa.

FIGS. 11 and 12 show sectional representations of a variant of the catch mechanism according to FIGS. 2 and 4. In the upper representation, the actuation element is in the setting according to FIG. 2, and the catch segments 22 are both in engagement by their form-fit elements 23 with the locking elements 40. In addition, the catch elements 50, which are pressed outward by the compression spring 55, are located in recesses or depressions in the form of grooves as a form-fit component of the locking elements 40, so that the catch mechanism is held in the regulating position by the actuation elements 70. FIG. 12 represents the fully released and opened position, as is also represented in FIG. 4. The catch elements 50, which may be configured as pins with spherical heads, engage into the form-fit component 45 on the outer circumference of the locking element 40 and hold the latter in the release position, in which the form-fit elements 23 of the catch segments 22 are brought out of engagement with the locking elements 40.

The invention claimed is:

1. A prosthetic wrist, comprising:

a base for fastening to a proximal prosthesis component; and a pivot part mounted on the base such that it is pivotable about a pivot axle;

at least one fastening device for securing a distal prosthesis component or prosthetic hand to the pivot part;

at least one catch segment with form-fit elements arranged thereon, wherein the at least one catch segment is arranged on the pivot part;

at least one locking element is mounted on the base such that it is longitudinally displaceable along the pivot axle from a locked setting, in which the at least one locking element is in engagement with a form-fit element of the form-fit elements of the at least one catch segment, against at least one spring force, to a plurality of release settings including a first release setting and a second release setting, wherein the at least one locking element has two release regions including a first release region wherein the first release setting is implemented and a second release region wherein the second release setting is implemented, wherein in that the first release region is arranged spaced apart from the second release region in a displacement direction, and wherein at least one catch element is configured to hold the at least one locking element in the second release setting is assigned to the second release region.

2. The prosthetic wrist as claimed in claim 1, wherein the at least one locking element in the first release setting is displaceable into the second release setting against the at least one spring force and into the locked setting by the spring force.

3. The prosthetic wrist as claimed in claim 1 wherein the at least one spring force comprises a first spring force against displacement and a second spring force against displacement, wherein the first spring force against displacement into the second release setting is greater than the second spring force against the displacement into the first release setting.

4. The prosthetic wrist as claimed in claim 3, wherein the first spring force against displacement into the second release setting at the start of the second release region is at least 10% greater than the second spring force against the displacement of the first release region at the end of the first release setting.

5. The prosthetic wrist as claimed in claim 1 wherein the at least one locking element is braced in relation to the base by at least one spring element against displacement into at least one a-release setting of the plurality of release settings.

6. The prosthetic wrist as claimed in claim 5, wherein the at least one spring element is configured in two stages, with a stepped or progressive spring characteristic, and/or wherein the at least one spring element comprises a plurality of spring elements arranged in the displacement direction of the at least one locking element such that the plurality of spring elements can be brought successively into engagement.

7. The prosthetic wrist as claimed in claim 1 wherein the at least one locking element is assigned two actuation elements, wherein the two actuation elements lie opposite each other in the displacement direction.

8. The prosthetic wrist as claimed in claim 1 wherein the at least one locking element comprises two parallel-oriented locking elements mounted on the base on either side of the pivot axle.

9. The prosthetic wrist as claimed in 1 wherein both first release region and the second release region of the at least one locking element are configured as flats or reductions in diameter.

10. The prosthetic wrist as claimed in claim 1 wherein the at least one catch segment is configured in a form of a circle segment.

11. The prosthetic wrist as claimed in claim 1 wherein the form-fit elements are arranged or formed on a circumference of the at least one catch segment.

12. The prosthetic wrist as claimed in claim 1 wherein the at least one catch element is spring-loaded in a direction of the at least one locking element.

13. The prosthetic wrist as claimed in claim 1 wherein the at least one locking element has a form-fit component, and wherein the at least one catch element can be brought into engagement with the form-fit component of the at least one locking element.

14. The prosthetic wrist as claimed in claim 1 wherein the pivot part is mounted on the base such that it can pivot against a spring force.

15. The prosthetic wrist as claimed in claim 14, wherein the pivot part is held in an initial setting by at least one spring component which is configured to act in opposite directions.

16. The prosthetic wrist as claimed in claim 15, wherein the at least one spring component includes a plurality of spring components, wherein the plurality of the spring components are arranged in recesses on the base or the pivot part, and wherein the plurality of spring components are braced on abutments on a respectively opposite element.

17. The prosthetic wrist as claimed in claim 16, wherein each abutment of the abutments is configured as a bushing secured to the at least one catch segment or the base.

18. The prosthetic wrist as claimed in claim 15 wherein the at least one spring component is arranged on a stop and an abutment is configured to be brought away from the stop out of engagement with the at least one spring component.

* * * * *